United States Patent [19]

Rommel et al.

[11] 4,158,779
[45] Jun. 19, 1979

[54] X-RAY SHIELD

[75] Inventors: Werner Rommel; Franz Starp, both of Wildbad, Fed. Rep. of Germany

[73] Assignee: Prontor-Werk Alfred Gauthier GmbH, Fed. Rep. of Germany

[21] Appl. No.: 854,855

[22] Filed: Nov. 25, 1977

[30] Foreign Application Priority Data

Nov. 27, 1976 [DE] Fed. Rep. of Germany ....... 2653998
Oct. 7, 1977 [DE] Fed. Rep. of Germany ....... 2745123

[51] Int. Cl.² .............................................. G21F 5/00
[52] U.S. Cl. .................................... 250/515; 250/505
[58] Field of Search ................ 250/515, 516, 505, 510

[56] References Cited

U.S. PATENT DOCUMENTS

| 2,506,342 | 5/1950 | Burke | 250/510 |
| 3,569,712 | 3/1971 | Avakoff | 250/510 |
| 3,723,743 | 3/1973 | Brackenbrough et al. | 250/515 |

FOREIGN PATENT DOCUMENTS 1214707 12/1970 United Kingdom ..................... 250/515

Primary Examiner—Bruce C. Anderson
Attorney, Agent, or Firm—Arthur A. March

[57] ABSTRACT

A shielding device for the protection of human embryo cells from the effects of radiation during examination by X-ray comprising a radiant absorbent protective screen rotatably secured to a supporting frame, the screen including a central protective plate of predetermined shape; a first plurality of protective displaceable sheets, a second plurality of protective sheets associated with said first protective sheets mounted in pairs and being rotatable on one pair of said first sheets and adjusting means to linearly displace the first protective sheets to vary the covering surface area of the screen.

15 Claims, 10 Drawing Figures

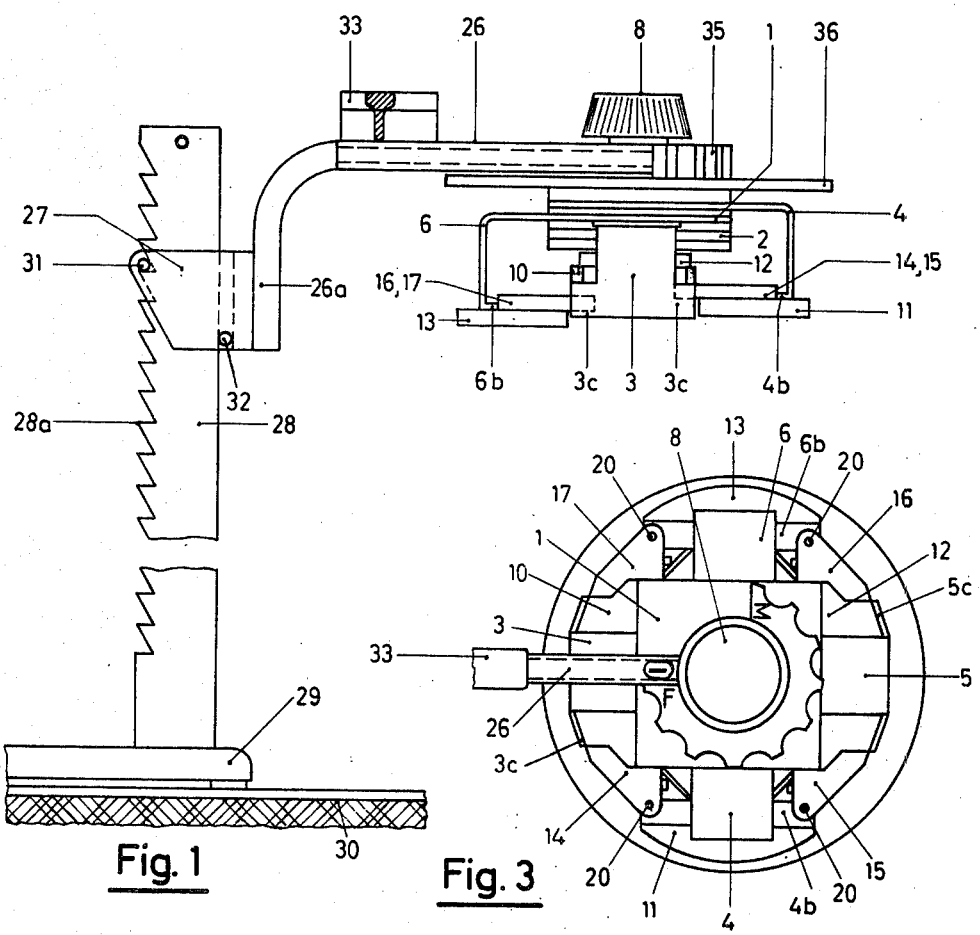
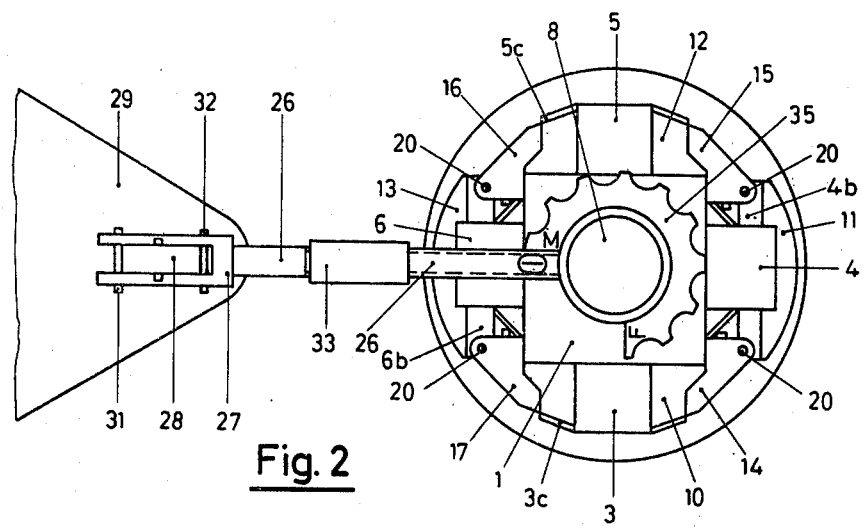
Fig. 1
Fig. 2
Fig. 3

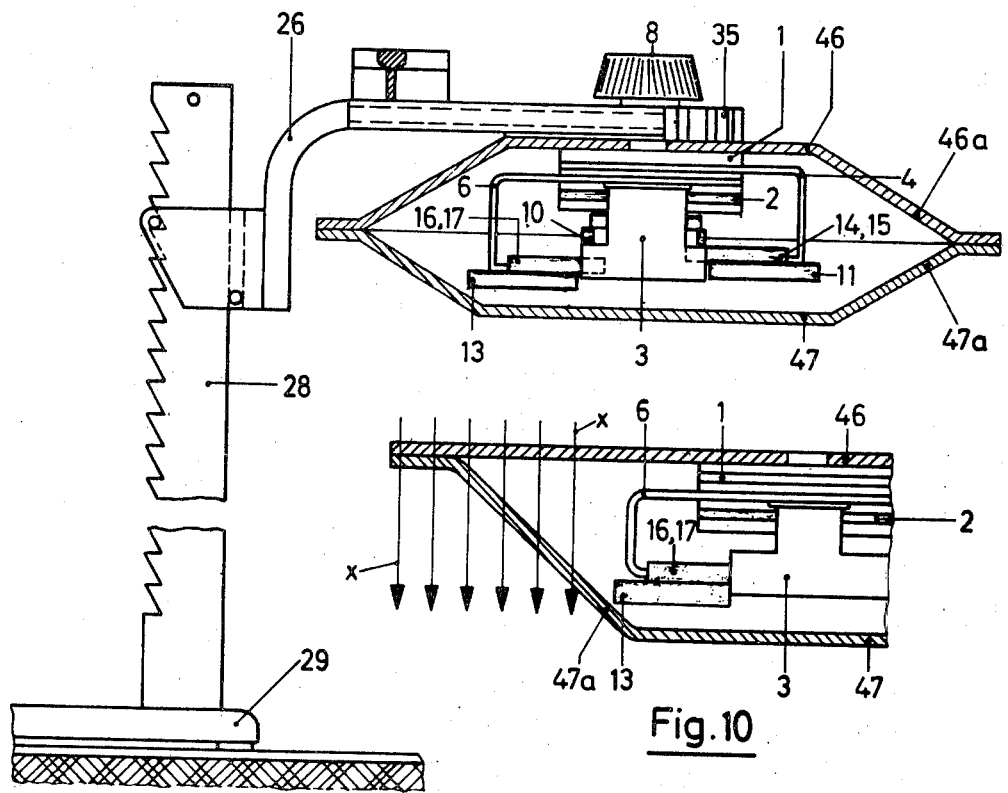
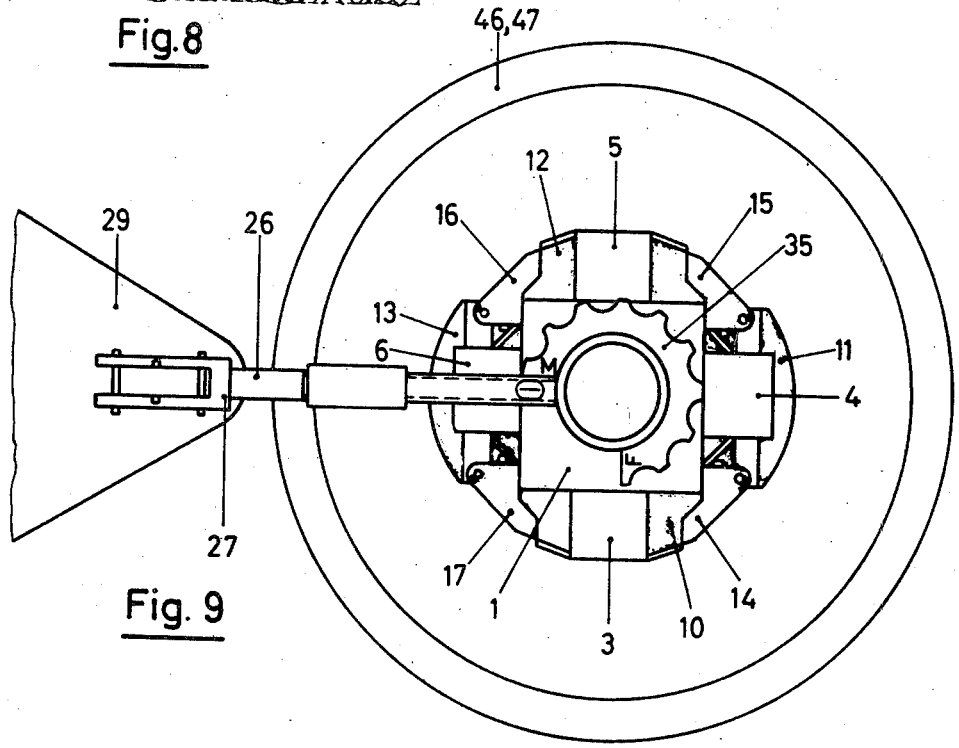
Fig. 8
Fig. 10
Fig. 9

X-RAY SHIELD

The present invention broadly relates to shields used for the protection of human embryo cells against the effect of that radiation which is produced during exposure to X-rays.

Heretofore, in order to attempt to solve the problems relating to X-ray exposures, it has been customary to use a structure which comprises a combination of two semi-circular leather pouches, joined together in the manner of a fan and containing lead shot. This structure has been used particularly for the local screening of the gonad region of the body which, because of danger to embryo cells, must be shielded from this radiation. Thus, the area of the body which must be protected from exposure to X-rays is covered by lead sheets to prevent the biological action of X-rays which, as is well known, is based upon absorption of the rays by the tissues.

Disadvantages of this traditional method of screening reside in the complicated and difficult manipulation of the flexible lead sheets to be applied to the body of the person to be X-rayed and in the fact that this method does not provide infallible protection against radiation because of the fact that displacement or slipping of the lead sheets from the place of application may occur. In view of the harmful effects which may result from exposure of which the radiologist is unaware, a method of protection from radiation fulfilling safety requirements and applicable to adults and children of both sexes has been the subject of a long need by the medical profession.

Other attempts to solve the problems have been proposed. For example, a sheet of material, transparent to both light and X-rays and having a variety of screening segments of different shape and size, is mounted on the X-ray tube in such a manner that an appropriate one of the segments may be positioned in the path of the light or X-ray beams for shadowing the area to be protected. Another proposal utilizes a generally triangular lead shield having a handle bar extending from its base. The shield is slideable and rotatable through adjustment means on the free end of a telescopic element, which in turn is rotatably mounted on the housing of an x-ray tube. With this arrangement the shield may be adjusted vertically or horizontally in the path of the X-ray beam and the shaded area can be varied by turning the shield about the axis of the handle bar.

The object of the present invention is to provide a device which insures reliable and optimal screening of that part of the body which is to be protected from the effects of radiation during the carrying out of X-ray exposures, while nonetheless being manipulatable with ease and facility.

The present invention provides a shielding device for the protection of human embryo cells from the effects of radiation during examination by an X-ray machine, which comprises in essence, a protective screen for absorbing radiation which is rotatably secured to a supporting frame. The screen comprises a central protective plate of predetermined shape and a first plurality of additional lead sheets which are linearly displaceable by means of adjusting means such as gears to vary the covering surface area of the screen. Thus, additional lead sheets are controllable dependent on the displacement.

An inestimable advantage of the structural arrangement of this protecting device resides in its smooth manipulability in every respect. In addition, there can be no unintentional or unnoticed change of the basic position of the protective screen relative to the part of the body which is to be protected from the X-rays. In fact, there is little if any possibility of inadvertent or unnoticed change of the screen position since the support for the covering surface comprises a frame which when placed on the X-ray table, imparts such stability to the screen that it cannot be influenced by the movements of the person being subjected to the X-rays. In addition, by simple operating processes optimal conditions concerning the adaptation of the covering surface to the surface expansion of the part of the body to be shielded from the effect of the X-rays may be achieved with the device of the present invention.

A preferred embodiment of the invention provides structure for increasing or reducing the area to be covered by the protective screen by means of pairs of sheets of lead which are utilized to extend in planes at right angles to each other. Other layers of lead associated therewith are rotatably mounted in pairs on one pair of sheets and are freely and slidably supported at their free ends by means of spring pressure on control cams formed on the other pair of sheets. In order to cause the lead sheets to effect an expansion or reduction movement continuously and uniformly in any direction during adjustment, the linearly displaceable pairings of lead layers are secured in synchronous and oppositely displaceable fashion individually to holders associated with the adjusting gears. The holders are preferably designed as slides for this purpose and are provided with a rack-type extension. The teeth of the rack mesh with a pinion to accomplish the displacement of all linearly displaceable lead sheets and the rack is actuated by the rotation of a knob.

Favorable conditions for the variability of the protective screen over a wide range is achievable in a simple manner by means of a structure in which pairings of linearly displaceable associated lead sheets are arranged in different planes of movement. This arrangement permits the layers to slide together in such fashion as to permit overlapping of the parts and the resultant reduction of the surface area of the protective screen so that the application of said screen is practical for the X-raying of children and infants as well as for adults.

In order to provide conditions for the universal application of the protective device in connection with X-ray exposures of persons of both sexes, the structure of the present invention also provides that the displaceable sheets of lead form in combination with the center lead plate, a protective screen of elliptical shape and this shape is retained over the entire range of adjustment. Further, the protective screen, which is formed of a lead plate and a plurality of lead sheets, may be displaceable as a unit between two alternative positions which differ from each other by an angle of 90°. This is done by means of a manually operated adjusting device. This accomplishes the beneficial result that the protective device can be brought by a simple adjustment into the particular position in which the device offers optimal conditions for the protection of embryo cells of persons of either sex.

When making X-ray films, in order to adapt the protecting device in a simple manner to the various requirements for observing the most favorable distance of the X-ray tube from the area of the body to be protected, the protecting screen is secured to a supporting arm mounted so as to be vertically adjustable on a column. To insure the adjustability of the protecting device in a horizontal plane, the supporting arm may be constructed in telescopic form. According to a further concept of the present invention, the protecting screen may be mounted in another manner, i.e. on a pivot arm formed as a parallelogram guide if the simple adjustability of the protecting screen is insured relative to the area of the body to be screened.

Further, in accordance with the present invention, the protecting screen may be protected by a completely enclosing housing or casing. The casing may comprise an upper and a lower part, at least one of these parts being provided with a conical surface inclined in the direction of radiation. In this manner, sufficient security of the adjusting and screening mechanism from harmful external influences is accomplished. Also by avoiding different thicknesses of material in the formation of the casing, no shadows are visible on the X-ray image which could have originated from a locally limited thickness in the material of the casing to be penetrated by the X-rays.

For achieving a configuration of the casing suitable for production and also allowing for the functional requirements in an advantageous manner, the casing is formed of two identical parts having the shape of a plate and these two parts are correspondingly provided on their edges with an annular contact surface which connects them together. A special advantage of this construction resides in the fact that only one die or the like has to be prepared for moulding of both parts.

While it is not absolutely necessary for the actual purpose and operation of the above described structure, manipulation thereof is considerably facilitated and its operation made clearer if both parts of a casing are of transparent material, such as plexiglass or the like. The advantage of such a construction resides in the fact that it enables the operator to see at a glance the surface expansion and relative position of the lead sheets without requiring attention to scales, marks or the like which otherwise serve to indicate the adjusting processes.

The present invention will be described further, by way of example, with reference to the accompanying drawings, in which:

FIG. 1 is a side view of a protecting device;

FIG. 2 is a plan view of the device of FIG. 1 in a position in which the protecting screen is adjusted for X-raying males;

FIG. 3 is a plan view of the protecting screen in a position for X-raying females;

FIG. 8 is a side view of the protecting device provided with a casing enclosing the adjusting mechanism for the lead sheets and the lead sheets themselves;

FIG. 9 is a plan view of the device of FIG. 8; and

FIG. 10 is a view of another embodiment of a casing for the adjusting and screening mechanism.

Figure 4:
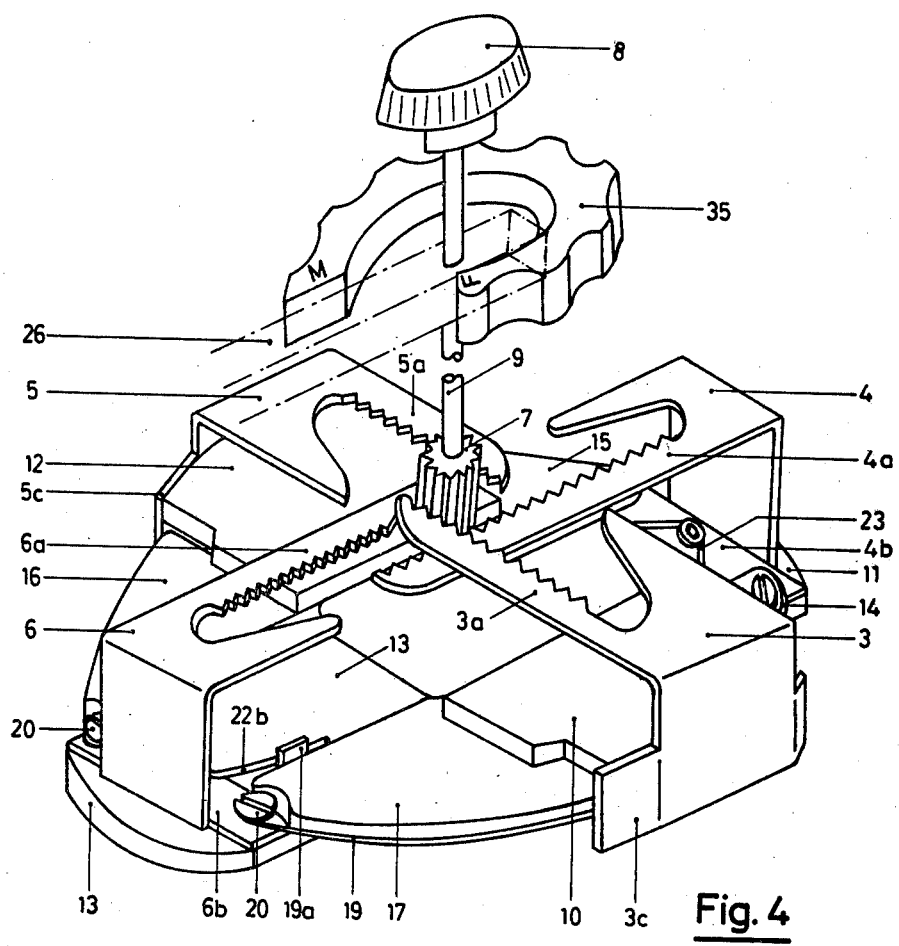
FIG. 4 is a perspective view of gear means for accomplishing the expansion or reduction of the protecting screen.

Referring specifically to the drawings, there is shown a plate assembly 1 which comprises a plurality of plates of thin metal or plastic material which are assembled in layers and between which a lead plate 2 of the same shape and about 2-3 mm thickness is interposed. A plurality of spacer strips arranged in pairs are inserted for forming guide slots. The arrangement of the spacer strips between the preferably square plates is effected alternately in different planes and in transverse directions extending at right angles to each other. The resultant guide slots extend over the total width of the plate assembly and in each case receive slides 3, 4, 5 and 6 and which, as shown in FIG. 4, are provided with a rack-like extension 3a, 4a, 5a, and 6a respectively. Engaging with the teeth formed on each extension is a pinion 7. The pinion 7 is non-rotatably mounted on an adjusting spindle 9 passing through a bore of the plate assembly 1. The spindle 9 is provided with a knob 8. Each slide 3-6 is provided with a downwardly extending portion at its end extending out of the plate assembly 1. The lower end of the downwardly extending portion is also bent inwardly at a right angle. The resultant strips 3b, 4b, 5b, and 6b serve for securing or supporting lead sheets 10, 11, 12 and 13, respectively. Varying the length of the particular downwardly extending portion enables the linearly displaceable lead layers to be disposed in parallel but different planes relative to the plane in which the center lead plate 2 is disposed. In addition to the linearly displaceable first lead sheets 10 to 13, segment-like lead sheets 14, 15, 16 and 17 are provided which serve to screen the corners. These second sheets are associated with each other in pairs and are arranged so as to rotate by means of respective support levers 19 and fixing screws 20 or the like on the particular securing strip 4b or 6b of the slide 4 or 6. For safety purposes, to avoid apertures such as bores or the like on the first lead sheets 10 to 13, the connection of said sheets with the support slides 3 to 6 and the connection of the lead sheets 14 to 17 with the particular support lever 19, are effected by means of a contact adhesive suitable for metal adherence.

Figure 5:
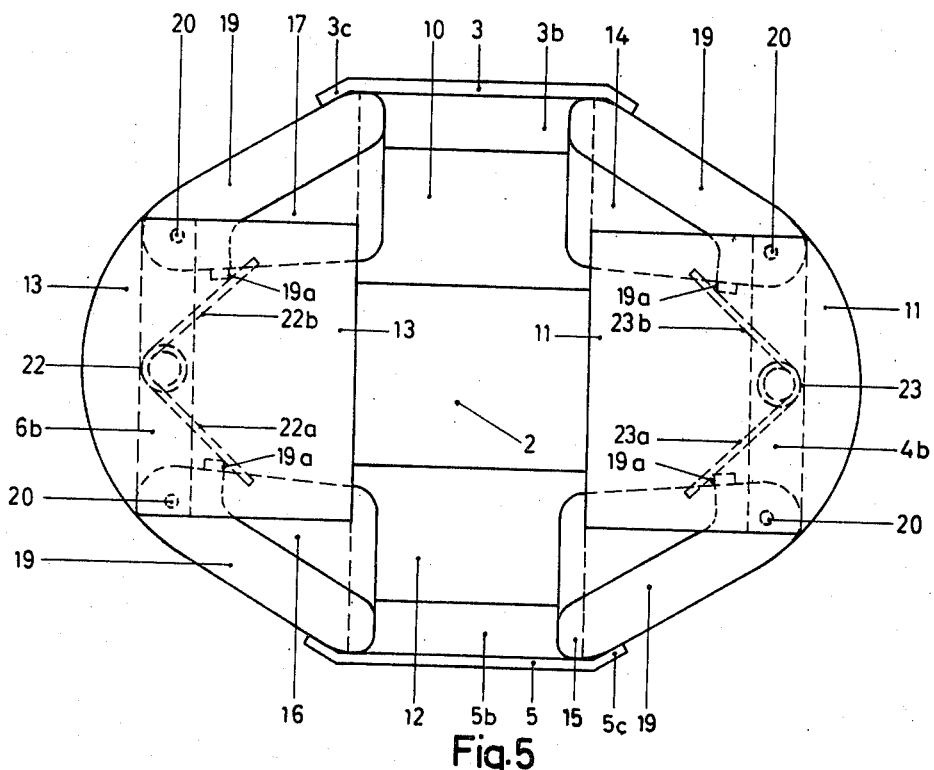
FIG. 5 is a view of the underside of the protecting screen adjusted to the maximum area to be covered.
Figure 6:
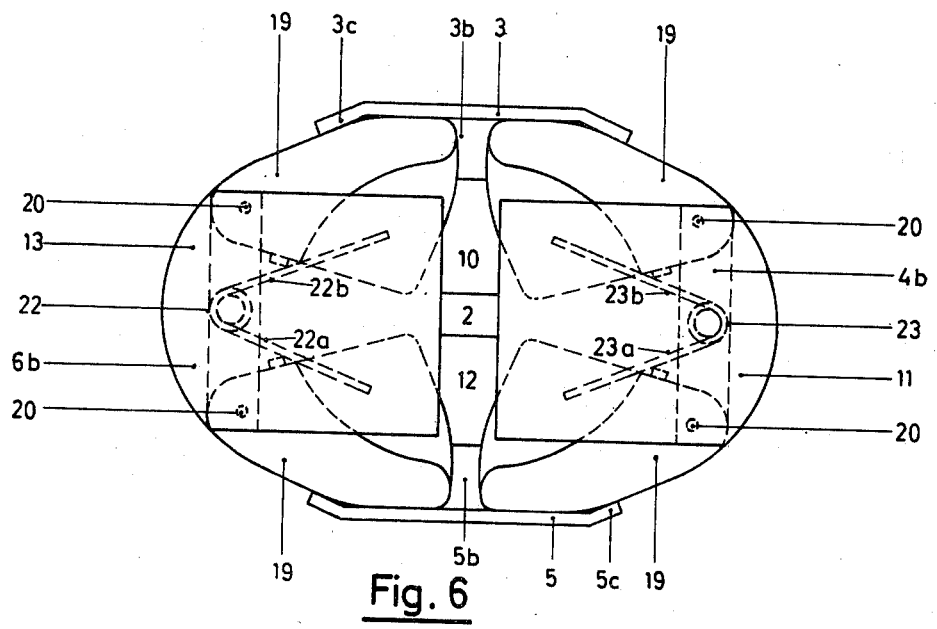
FIG. 6 is a view of the protecting screen as in FIG. 5 but adjusted to the minimum area to be covered.

The segment-like lead sheets 14 and 15 or 16 and 17 are associated with each other in pairs and are under the influence preferably of respective double-shank spiral springs 22 and 23. These springs are disposed on the respective securing strips 4b and 6b. The shanks 22a and 22b or 23a and 23b of springs 22 and 23 engage on lugs 19a formed on the respective support levers 19 and consequently exert an oppositely directed torque on the pairs of lead sheets 14 and 15 or 16 and 17 relative to their centers of rotation. The spring load acting on the lead sheets is received by guide lugs 3c and 5c which, as shown in FIGS. 5 and 6, are formed on the slides 3 and 5. The lugs are provided for slidably guiding the sheets 14 and 15 or 16 and 17 which are supported by their free ends. Relative movement in opposite directions is accomplished by the associated pairs of lead sheets when the holders or slides 10 to 13 which are guided displaceably in the guide slots of the plate assembly 1, are driven by the pinion 7.

According to the direction of rotation of the pinion 7, the sheets 10 and 12 or 11 and 13, supported by the slides 3 and 5 or 4 and 6 move either continuously towards or away from each other. This also applied to the lead sheets 14 and 15 or 16 and 17 which cover the corner cut-outs and rest under spring load on the guide lugs 3c and 5c of the slides 3 and 5. The latter lead sheets slide along when the slides 3 to 6 are executing relative movement, in which they simultaneously execute rotations about their pivotal axis. In turn, such movements result in either an expansion or reduction on all sides of the area to be covered by the protecting screen completely formed of lead sheets, while the function of covering the "opening" in the area of the plate assembly 1 is effected by the center lead plate 2.

In order to achieve a reduction in the area to be covered by the protecting screen formed of the displaceable lead sheets 10 to 17, so that the operating conditions are also available in these instances where only a small surface area has to be screened, e.g. for a child, an arrangement of the linearly displaceable lead sheets 10 to 13 is provided, as is clearly seen in FIG. 1. Conditions could therefore be provided in which the lead sheets 10 to 17 may be moved towards each other and overlapping to form an extremely small protecting screen, as shown in FIG. 6.

The protecting screen, whose construction is described above, is formed by the center lead plate 2 and the displaceable lead sheets 10 to 17. The screen is held by a support arm 26 which may be telescopic and secured to a supporting fork 27 by means of bent-over portion 26a. The fork 27 is vertically adjustable relative to a vertical support column 28. This column 28 may be secured in upright fashion on a preferably metal triangular base plate 29. The arrangement of the support column 28 on the base plate 29, is, as shown in FIG. 2, effected so that the protecting device may be set rigidly on the X-ray table 30, as shown in FIG. 1. In order to adapt the vertical adjustment of the protecting screen to the prevailing conditions, the support column 28 is provided on one edge with a locking device 28a which may have a saw-tooth profile, as shown in FIG. 1, or a semi-circular or any other suitable profile. In turn, the support fork 27 is provided with a pin which provides a hooking engagement with the saw-tooth profile 28a of the column 28 by means of another pin 32 supported on the smooth edge of the support column 28. A tilting movement is sufficient for adjusting the vertical position of the protecting screen and this is effected by slightly raising the support arm 26 in order to bring the pin 31 of the support fork 27 out of engagement with the locking arrangement 28a. Thus the protecting screen can be brought to a different vertical position by raising or lowering the support arm 26 and then re-secured by engaging the cross pin 31 in the locking arrangement 28a in the new vertical position. As a consequence, when the support arm 26 is released, the pin 32 as shown in FIG. 1, under the influence of gravity, becomes disposed again on the smooth edge of the support column 28, and, as a result, the pin 31 is firmly drawn into the teeth 28a and maintained in engagement. Easier manipulation of the supporting frame 26 to 28 may be obtained for vertical adjustment if the support arm 26 is provided with a handle 33 having a T-shaped cross-section.

As may be seen more particularly from the illustrations in FIGS. 1 to 3, two different basic positions are provided for the protecting screen which are indicated by "M" (male) and "F" (female). The characteristic difference in these two basic positions resides only in the fact that, in position "M," the longer axis of the protecting screen, of elliptical shape, is aligned with the support arm 26, whilst in the other adjustment "F" the longitudinal axis of the ellipse extends transversely to the support arm 26. For this purpose the protecting screen as a whole is mounted to rotate about a vertical axis, on the shaft 9 on the end of the support arm 26. By means of an adjusting ring 35, preferably having a segment-like cut-out, as shown in FIGS. 2 and 3, the screen is adjustable between positions "M" and "F." The basic positions differ from each other by an angle of 90°. The adjusting ring 35 is preferably connected securely to the plate assembly 1 by a screw connection or the like, and is associated with the support arm 26 so that the latter can assume the function of a stop limiting the rotation of the adjusting ring 35 both in one direction and the other. A circular disc preferably of plexiglass is indicated by the numeral 36, the purpose of which is primarily to protect the displaceable and rotatable parts of the protecting screen, such as slides, support levers and lead sheets carried thereby.

Figure 7:
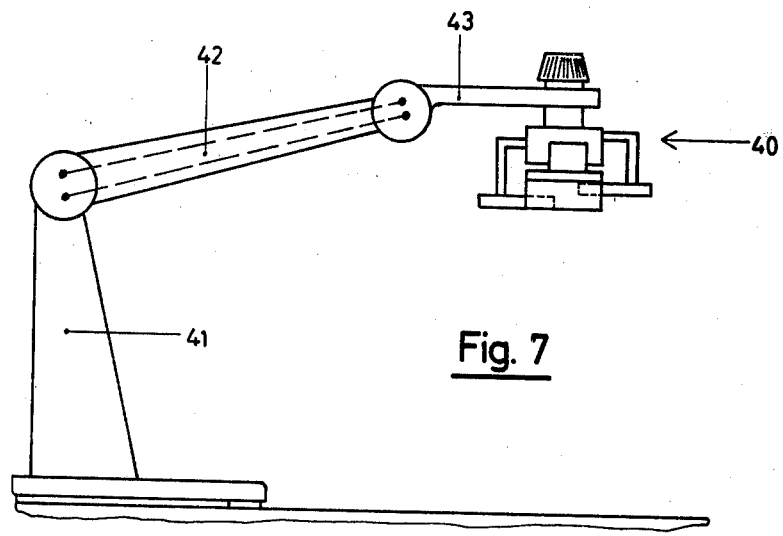
FIG. 7 is a view of a modified form of supporting frame for the protecting screen.

According to the arrangement of FIG. 7, a supporting frame for a protective screen may also be provided by means of a guiding member 42 arranged to be rotatable on a support 41 and preferably by the form of a parallelogram guide. In addition, the outer end of this guide could have a rotatably secured support arm 43 for the suspension of the protective screen, thus ensuring that the screen always retains a horizontal position in any adjusted vertical position.

In order to ensure that the above described setting and screening mechanism is protected against harmful effects, such as from soiling after a comparatively long period of use, or even when the operators do not provide appropriate care and attention to the apparatus, it is possible to hermetically seal the entire mechanism, in a casing. This casing may, as shown in FIGS. 8, 9 and 10, be formed of upper and lower portions 46 and 47. The portions are joined together at the edges, preferably by means of a contact adhesive or the like. The shape of the casing itself may be accomplished in accordance with the embodiment shown in FIG. 10. As shown, a part 46 is constructed as a flat disc and another part 47 has a surface 47a extending at an incline in the direction of radiation X of the X-ray machine. It is important that the angle of incline of the conical surface 47a of the part 47 should be shallow so that the degree of penetration of the X-rays does not experience any appreciable increase. An angle of incline of less than 30° is necessary for this purpose.

According to the other embodiment shown in FIGS. 8 and 9, the casing may also consist of two identical parts 46 and 47 each having a plate-like shape. Both parts, similar to the parts of the casing shown in FIG. 10 are preferably made of transparent material, for example, plexiglass so that they can be moulded in a simple manner, by heating the material in a die or the like. If both parts 46 and 47 or at least one of them (FIG. 10) is provided on the edge with an annular contact surface, this facilitates joining or connecting the parts together by the application of contact adhesives.

It is to be understood that while the invention has been described in some detail, this is only for the purpose of facilitating an understanding thereof and is not at all intended to limit the scope of the invention as defined in the appended claims.

What is claimed is:

1. Shielding device for the protection of human embryo cells from the effects of radiation during examination by X-rays comprising a radiant absorbing protective screen including a central radiant absorbing protective plate of predetermined configuration, a plurality of additional radiant absorbing protective displaceable sheets and adjusting means to displace the sheets relative to each other to vary the covering surface area of the screen.

2. Device according to claim 1 including a supporting frame to which the protective screen is rotatably secured for rotation of the screen within its own plane.

3. Device according to claim 2 wherein the plate and sheets are composed of lead.

4. Device according to claim 3 wherein the plurality of sheets comprises pairs of first lead sheets movable at right angles for enlarging or reducing the covering area of the protective screen and further including second lead sheets mounted in pairs and being rotatable operatively on one pair of the first sheets, pressure means for correspondingly rotatably biasing the second sheets, and cam members disposed on another pair of the first sheets on which the second sheets are freely and slidably supported.

5. Device according to claim 4 including holders associated with the adjusting means to which the pairs of sheets are secured, the pairs of sheets being synchronously and oppositely displaceable.

6. Device according to claim 5 wherein the holders comprise slides having a rack-like extension provided with teeth, a pinion for meshing with such teeth for displacement of all the sheets and a knob for rotating the pinion to displace the sheets.

7. Device according to claim 6 wherein the associated pairings of sheets are arranged in various movement planes, and all of the sheets are displaceable relative to each other in the direction of the corresponding planes of the sheets.

8. Device according to claim 1 including a closed casing completely enclosing the protective screen, the casing comprising an upper part and a lower part and having on one such part a conical surface inclined in the direction of radiation.

9. Device according to claim 8 wherein the casing comprises two identical parts of plate-like shape, the parts being joinable by an annular contact surface provided on the edges of such parts.

10. Device according to claim 8 wherein the casing is composed of transparent material.

11. Shielding device for the protection of human embryo cells from the effects of radiation during examination by X-rays comprising a radiant absorbing protective screen including a central radiant absorbing protective plate of predetermined configuration, a plurality of additional radiant absorbing protective displaceable sheets and adjusting means to displace the sheets to vary the covering surface area of the screen, the central plate and displaceable sheets being arranged to provide a protective screen of elliptical shape which shape is retained over the entire range of adjustment of the adjusting means.

12. Device according to claim 11 including an adjusting ring for adjusting the entire protective screen comprised of the central plate and displaceable sheets between two alternative adjustments which deviate from each other by an angular displacement of 90 degrees.

13. Device according to claim 12 including a supporting arm to which the protective screen is connected and a support column for the supporting arm on which arm is vertically adjustable.

14. Device according to claim 13 wherein the supporting arm is a telescopically adjustable arm.

15. Device according to claim 12 including a pivot arm support for supporting the protective screen as a parallelogram guide.

* * * * *